United States Patent
Berkani et al.

(10) Patent No.: US 7,798,327 B1
(45) Date of Patent: Sep. 21, 2010

(54) MULTI-PACK SANITARY NAPKIN CONTAINER AND ASSOCIATED METHOD

(76) Inventors: Samir Berkani, 29 Route Ouled Fayet Cherage, Algiers (DZ) 16000; Farah M. Charles, 8A Forest Glen Rd., Valley Cottage, NY (US) 10969

( * ) Notice: Subject to any disclaimer, the term of this patent is extended or adjusted under 35 U.S.C. 154(b) by 404 days.

(21) Appl. No.: 11/973,931

(22) Filed: Oct. 11, 2007

(51) Int. Cl.
*A61B 17/06* (2006.01)
*B65D 85/16* (2006.01)

(52) U.S. Cl. .............. 206/440; 206/494; 53/443; 53/467; 229/113; 229/116.1

(58) Field of Classification Search .......... 206/438, 206/440, 441, 494, 581; 53/443, 467, 469, 53/474; 229/113, 116.1, 193; 604/385.01–385.05
See application file for complete search history.

(56) References Cited

U.S. PATENT DOCUMENTS

| | | | | |
|---|---|---|---|---|
| 2,072,753 A | * | 3/1937 | Ikeda et al. | 229/113 |
| 2,312,507 A | * | 3/1943 | Trogman | 229/113 |
| 3,078,989 A | * | 2/1963 | Curran et al. | 206/440 |
| 4,378,905 A | * | 4/1983 | Roccaforte | 229/193 |
| 5,014,905 A | * | 5/1991 | Cassidy | 229/113 |
| 6,923,321 B2 | * | 8/2005 | Samolinski et al. | 206/440 |
| 2002/0063136 A1 | * | 5/2002 | Sauer et al. | 206/494 |
| 2002/0148749 A1 | * | 10/2002 | Briseboi et al. | 206/440 |
| 2004/0102748 A1 | * | 5/2004 | Hirotsu | 206/438 |
| 2007/0119913 A1 | * | 5/2007 | Holley | 229/116.1 |

* cited by examiner

*Primary Examiner*—Luan K Bui

(57) ABSTRACT

A multi-pack sanitary napkin container includes a flexible outer container and first, second, third, and fourth pluralities of sanitary napkins respectively. Such first, second, third, and fourth pluralities of sanitary napkins are vertically stacked within an interior portion of the container. The kit further includes a mechanism for securing the container about the first, second, third, and fourth pluralities respectively of sanitary napkins when the first, second, third, and fourth pluralities of sanitary napkins are vertically stacked within the interior portion of the container.

12 Claims, 5 Drawing Sheets

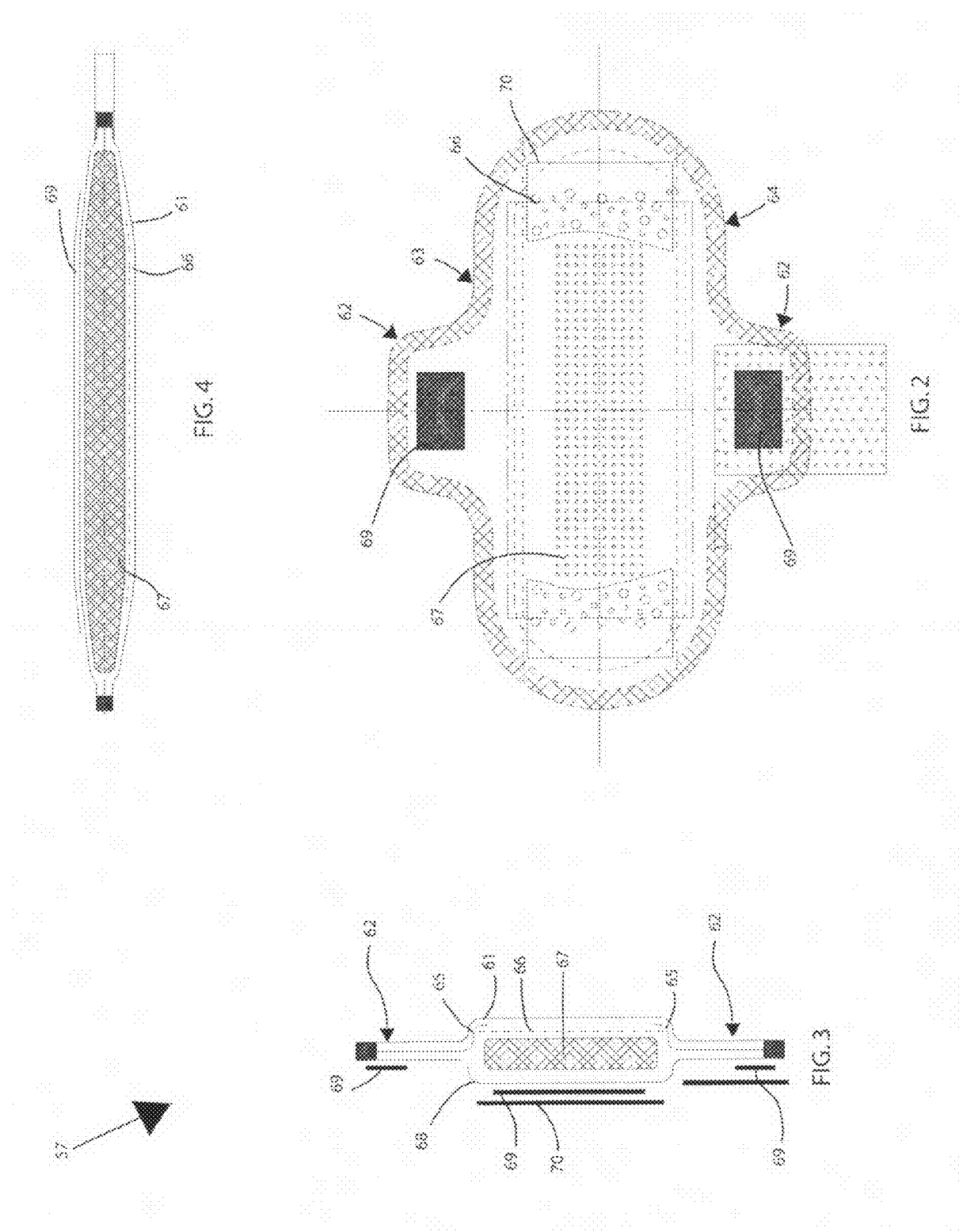

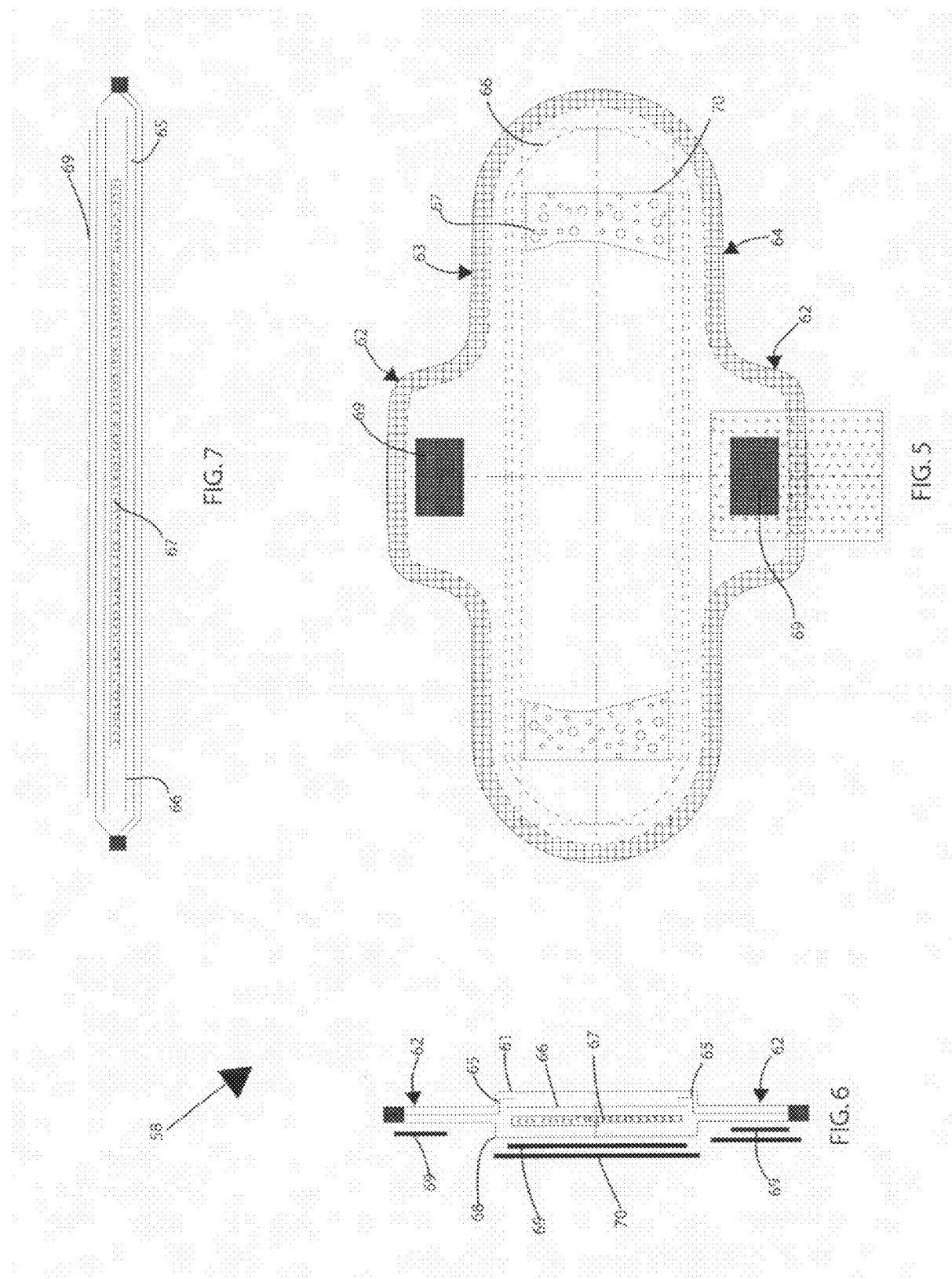

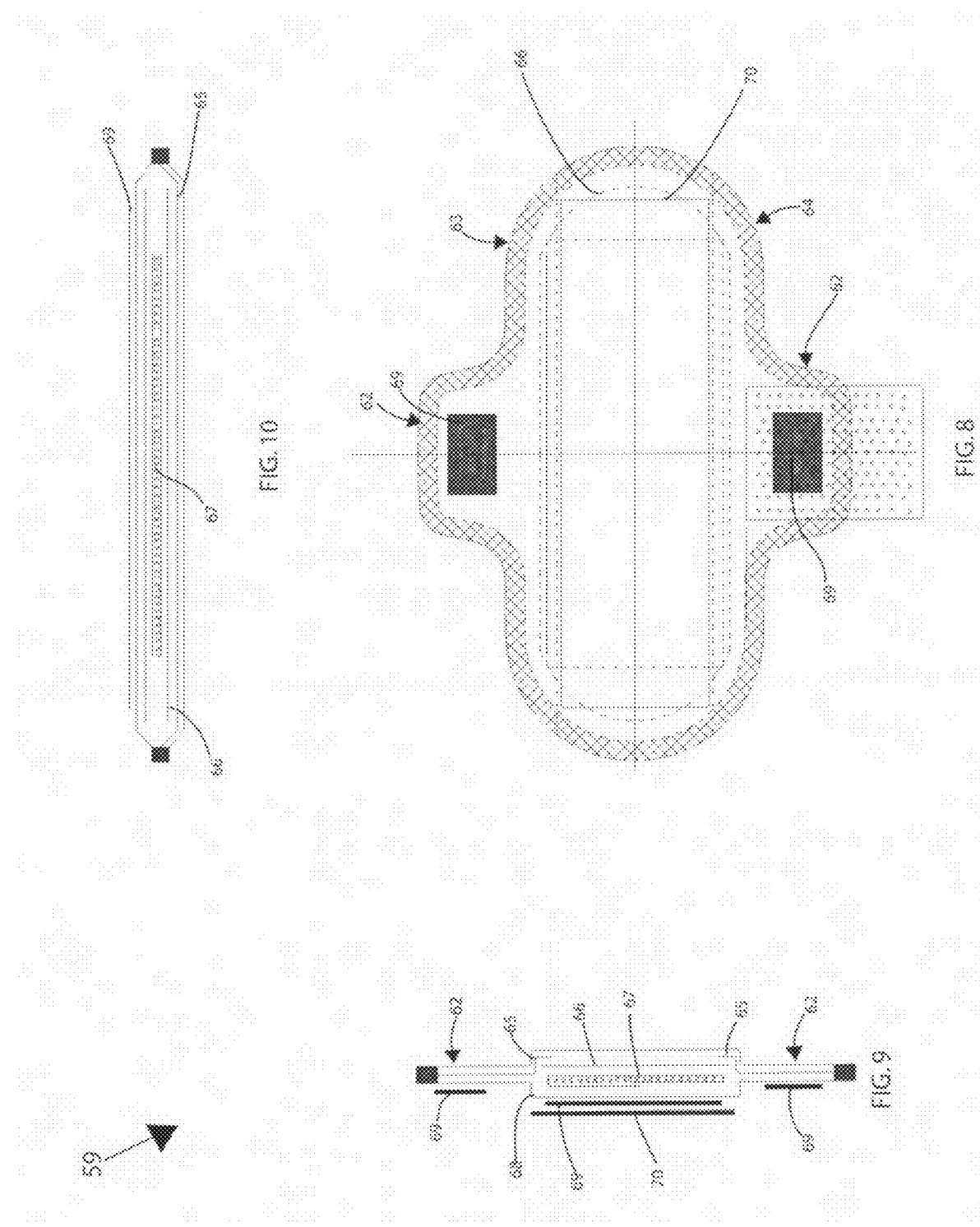

MULTI-PACK SANITARY NAPKIN CONTAINER AND ASSOCIATED METHOD

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to sanitary napkins and, more particularly, to a multi-pack sanitary napkin container for providing a plurality of differently sized sanitary napkins for use during different periods of the user menstrual cycle.

2. Prior Art

There are various types of feminine sanitary napkins: slims, ultra slims, wings, no wings, regular absorbency, night time absorbency, and heavy flow days and nights. These products are available with different length pads to meet the needs of all women and to provide the right protection for each day of their menstrual cycle. The purchase of so many different types of products is often very expensive, but necessary to allow a woman to cover each of her needs during a menstrual cycle. There is therefore a need for combining several feminine hygiene products into one convenient package, thereby eliminating the need for a user to purchase several absorbency levels of sanitary napkins.

U.S. Pat. No. 7,144,391 to Kreutz discloses a kit comprised of feminine hygiene products. In particular, this kit may be used as learner kits are disclosed. Such kits preferably include at least an absorbent tampon having an absorbency of less than or equal to about 6 grams according to the syngina test. Also included with the kit is a backup feminine hygiene article such as a pantiliner, sanitary napkin, or absorbent interlabial device. Other optional components such as a mirror, finger cover, glove, lubricant, bonus product, and/or an instruction booklet, may also be included in the kit. Also disclosed are non-absorbent training tampons which may be used to assist a new tampon user in getting the feel for proper tampon insertion technique. Unfortunately, this prior art example is not designed to provide protection for an entire menstrual cycle.

U.S. Pat. No. 6,183,456 to Brown discloses an absorbent interlabial device worn by female wearers for catamenial purposes, incontinence protection, or both. The absorbent interlabial device includes a liquid pervious topsheet, a liquid impervious backsheet, and an absorbent core positioned between the two. The length of the device is between about 60 mm and about 130 mm. The width is between about 25 mm and about 50 mm. The device has an axis of preferred bending along its longitudinal centerline. When folded along the axis and inserted into the wearer's interlabial space, the topsheet maintains contact with the walls of the wearer's labia. A method of using a system of feminine hygiene products is also disclosed. The system includes the use of an absorbent interlabial device in combination with a sanitary napkin. The absorbent interlabial device of the present invention may also be used in combination with an absorbent tampon. The absorbent interlabial device may be packaged in a common package with a sanitary napkin or a tampon as a feminine hygiene kit. Unfortunately, this prior art example does not provide a user with various products that may be used for varying needs during a single menstrual cycle.

U.S. Pat. No. 5,897,542 to Lash discloses a package containing absorbent articles having differing absorbent capacities. The package includes at least one first absorbent article with a predetermined absorbent capacity, and at least one second absorbent article with a predetermined absorbent capacity. The absorbent capacity of the second absorbent article is greater than the absorbent capacity of the first absorbent article. Unfortunately, this prior art example does not provide a user a complete array of articles needed for a full menstrual cycle.

Accordingly, the present invention is disclosed in order to overcome the above noted shortcomings. The present invention satisfies such a need by providing a kit that is convenient and easy to use, lightweight yet durable in design, and designed for providing a plurality of differently sized sanitary napkins for use during different periods of the user menstrual cycle. The kit consists of various types of sanitary napkins such as regular and with wings. The kit would also include panty-liners, intimate wipes, and several pairs of briefs. The main purpose of the kit is to provide a female user with all of the products necessary for one full menstrual cycle. The present invention is simple to use, inexpensive, and designed for use throughout a single menstrual cycle.

BRIEF SUMMARY OF THE INVENTION

In view of the foregoing background, it is therefore an object of the present invention to provide a kit for providing a plurality of differently sized sanitary napkins for use during different periods of the user menstrual cycle. These and other objects, features, and advantages of the invention are provided by a multi-pack sanitary napkin container.

A multi-pack sanitary napkin container includes a flexible outer container. Such a container is adjusted in size and shape respectively based upon the number of items contained therein. The container includes a substantially rectangular shaped and planar base with top, bottom, left, and right sides respectively. The container further includes first and second coextensively shaped wings monolithically formed with the left and right sides respectively of the base. Each of such first and second wings effectively extends outwardly and away from the base member.

The container further includes first and second coextensively shaped walls with bottom edges directly attached to the top and bottom sides of the base respectively. Each of such first and second walls conveniently has a top edge extending outwardly and away from the base. Such top edges have a lateral width that is less than a lateral width of the bottom edges, and each of the first and second walls has opposed arcuately shaped outer edges spanning between laterally opposed ends of the top and bottom edges respectively. The top and bottom edges of the first and second walls are oriented parallel to each other.

The container further includes first, second, third, and fourth coextensively shaped flaps with an inner edge monolithically formed with associated ones of the outer edges of the first and second walls respectively. Each of such first, second, third, and fourth flaps advantageously has an outer edge extending outwardly and away from the outer edges of the first and second walls respectively. The first and second flaps respectively have a notch formed in the outer edges thereof, and the second flap further has an opening formed therein. The third flap effectively has a tongue monolithically formed in the outer edge thereof and extending outwardly and away from the outer edge.

The container further includes a tab provided with top and bottom and left and right edges respectively. Such a bottom edge is directly attached to the top edge of the first wall, and such a top edge of the tab extends outwardly and away from the top edge of the first wall. The tab conveniently has a lateral width that is equal to the lateral width of the top edge of the first wall, and the top edge of the tab and the top edge of the first wall respectively are registered parallel to each other.

The container further includes first, second, and third coextensively shaped flanges monolithically formed with the left, top, and right edges respectively of the tab. Each of such first and third flanges advantageously has respective longitudinal lengths that are equal to a height of the tab, and such a second flange has a longitudinal length that is equal to the lateral width of the tab. The container further has first, second, and third panels attached along respective top and bottom longitudinal edges thereof. The top edge of the first panel is monolithically formed with the top edge of the second wall, and the top edge of the second panel is monolithically formed with the bottom edge of the first panel.

The top edge of the third panel is monolithically formed with the bottom edge of the second panel, and the first panel has a longitudinal length that is equal to the lateral width of the top edge of the second wall. Each of the first, second, and third panels effectively has equal longitudinal lengths and equal lateral widths respectively, and each of the respective top and bottom edges of the first, second, and third panels is registered parallel to each other. A series of apertures is conveniently formed in the top and bottom edges of the first and second panels respectively and the second and third panels respectively. Such apertures are equidistantly spaced along the top and bottom edges of the first and second panels respectively and the second and third panels respectively.

The kit further includes first, second, third, and fourth pluralities of disposable sanitary napkins vertically stacked within an interior portion of the container. Each of such first, second, and third pluralities of sanitary napkins respectively includes a top cover stock layer with a pair of tabs monolithically formed in respective upper and lower opposed edges thereof. Such tabs extend outwardly and away from the upper and lower edges respectively. The sanitary napkins further include a pair of side barriers attached to the cover stock layer and situated adjacent to the tabs, an acquisition layer attached to the side barriers and disposed medially thereof, and a liquid absorbent core member attached to the acquisition layer. Such a core member has a longitudinal length and a lateral width that are respectively less than a longitudinal length and a lateral width of the acquisition layer.

The sanitary napkins further include a backsheet positioned about the core member. Such a backsheet is suitably sized and shaped such that the acquisition layer and the core member and the side barriers are respectively intercalated between the backsheet and the cover stock. A glue layer is attached to spaced regions along the backsheet. Such a glue layer extends beyond an outer perimeter of the core member, and a bottom silicon paper layer is attached directly to the glue layer.

The backsheet and the core member are respectively liquid permeable while the acquisition layer and the side barriers and the cover stock layer are respectively liquid impermeable. Liquid from the user body is transferred to the core member via the liquid permeable layers respectively and penetrates therein. The liquid is absorbed and contained by the core member during operating conditions.

Each of the fourth plurality of sanitary napkins respectively includes a top barrier layer extending about a perimeter of the fourth plurality of sanitary napkins for preventing fluids from traveling beyond the perimeter. A polyethylene layer is attached to the top barrier and extends downwardly therefrom. Such a polyethylene layer is perforated for allowing fluids to enter therethrough. The fourth plurality of sanitary napkins further includes a fabric layer connected to the polyethylene layer, an absorbent core connected to the fabric layer, a fluid impermeable backsheet layer connected to the absorbent layer, a glue layer attached to the backsheet layer, and a bottom silicon paper layer removably attached to the glue layer.

The kit further includes a mechanism for securing the container about the first, second, third, and fourth pluralities respectively of sanitary napkins when the first, second, third, and fourth pluralities of sanitary napkins are vertically stacked within the interior portion of the container. Such a securing mechanism effectively includes a lip monolithically formed with the bottom edge of the third panel and extending outwardly and away therefrom. Such a lip has a longitudinal length that is equal to the longitudinal length of the third panel. The securing mechanism further includes a hook-and-loop type fastening material adhered to an inner surface of the lip such that the hook-and-loop type fastening material contacts an outer surface of the covering when the covering is folded about the vertically stacked first, second, third, and fourth pluralities of sanitary napkins. Such a fastening material conveniently prohibits the container from prematurely and undesirably unfolding during storage and transport procedures.

A method for providing a plurality of differently sized sanitary napkins employed during different periods of a user menstrual cycle includes the steps of: providing a flexible outer container; vertically stacking first, second, third, and fourth pluralities of sanitary napkins within an interior portion of the container; and securing the container about the first, second, third, and fourth pluralities of sanitary napkins after the first, second, third, and fourth pluralities of sanitary napkins are vertically stacked within the interior portion of the container.

The method further includes the steps of providing a lip monolithically formed with the bottom edge of the third panel and extending outwardly and away therefrom. Such a lip has a longitudinal length that is equal to the longitudinal length of the third panel. The steps further include providing a fastening material adhered to an inner surface of the lip such that the fastening material contacts an outer surface of the covering when the covering is folded about the vertically stacked first, second, third, and fourth pluralities of sanitary napkins. The fastening material prohibits the container from prematurely and undesirably unfolding during storage and transport procedures.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 2 is a top planar view of one of the first pluralities of sanitary napkins, in accordance with the present invention;

FIG. 3 is a cross sectional, front elevational view of one of the first pluralities of sanitary napkins, in accordance with the present invention;

FIG. 4 is a cross sectional, side elevational view of one of the first pluralities of sanitary napkins, in accordance with the present invention;

FIG. 5 is a top planar view of one of the second pluralities of sanitary napkins, in accordance with the present invention;

FIG. 6 is a cross sectional, front elevational view of one of the second pluralities of sanitary napkins, in accordance with the present invention;

FIG. 7 is a cross sectional, side elevational view of one of the second pluralities of sanitary napkins, in accordance with the present invention;

FIG. 8 is a top planar view of one of the third pluralities of sanitary napkins, in accordance with the present invention;

FIG. 9 is a cross sectional, front elevational view of one of the third pluralities of sanitary napkins, in accordance with the present invention;

FIG. 10 is a cross sectional, side elevational view of one of the third pluralities of sanitary napkins, in accordance with the present invention;

DETAILED DESCRIPTION OF THE INVENTION

Figure 1:
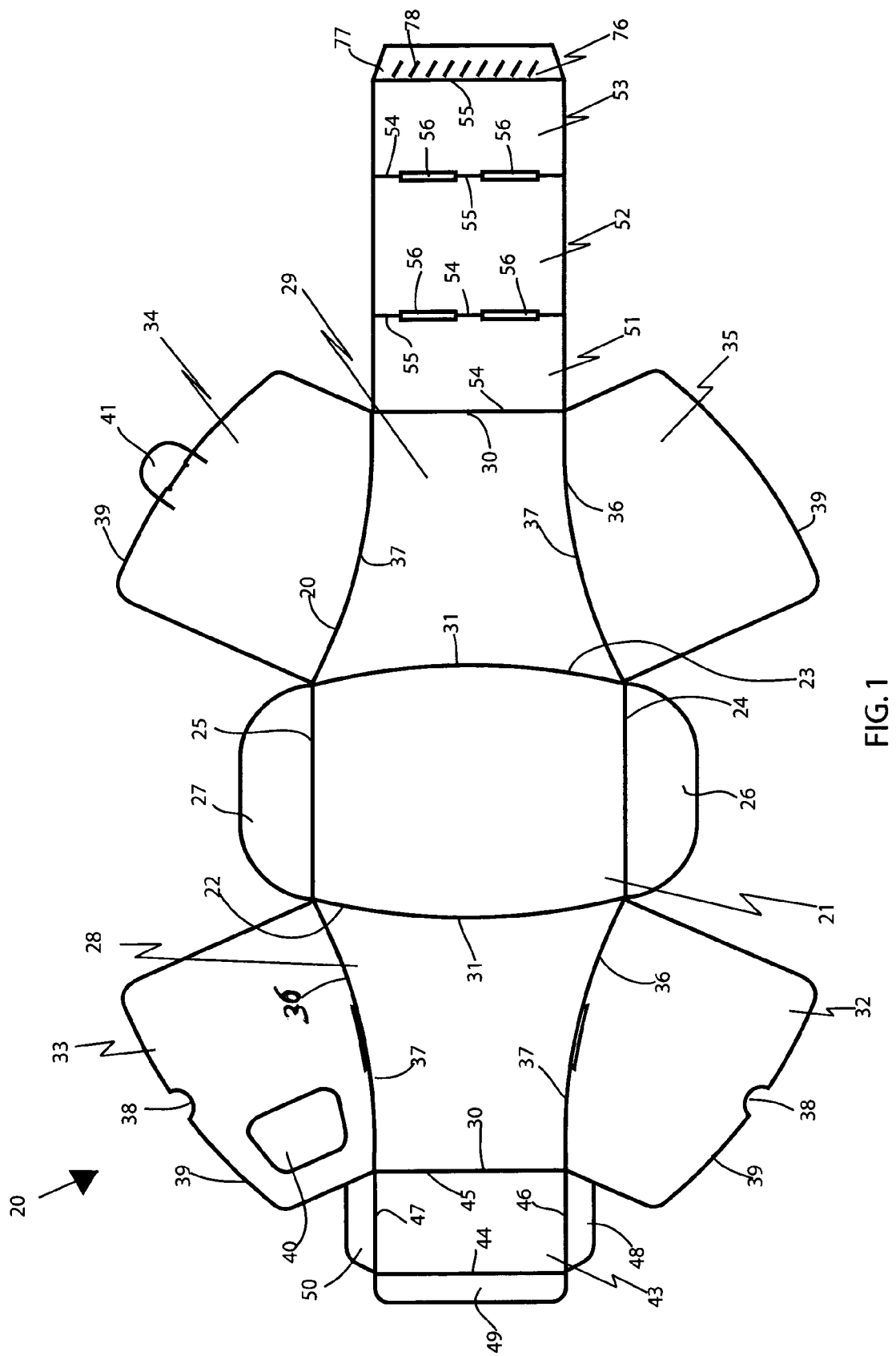
FIG. 1 is a top planar view of an unfolded container, in accordance with the present invention.
Figure 13:
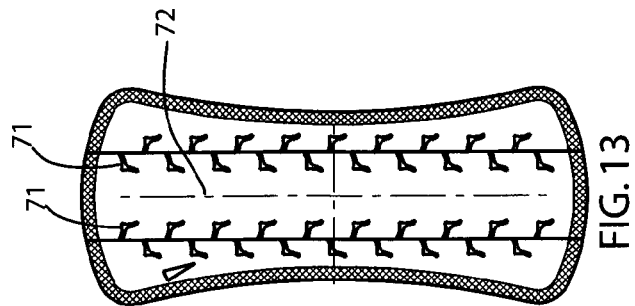
FIG. 13 is a top planar view of one of the fourth pluralities of the sanitary napkins, with the top barrier layer removed, in accordance with the present invention.
Figure 12:
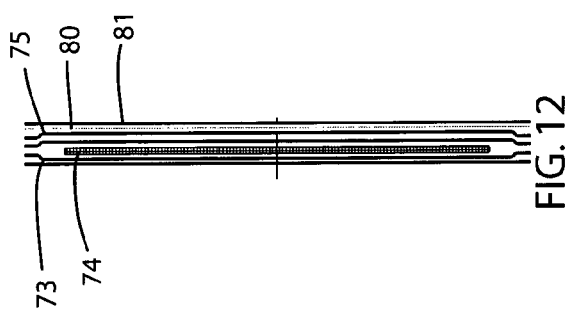
FIG. 12 is a cross sectional, side elevational view of one of the fourth pluralities of the sanitary napkins, in accordance with the present invention.
Figure 11:
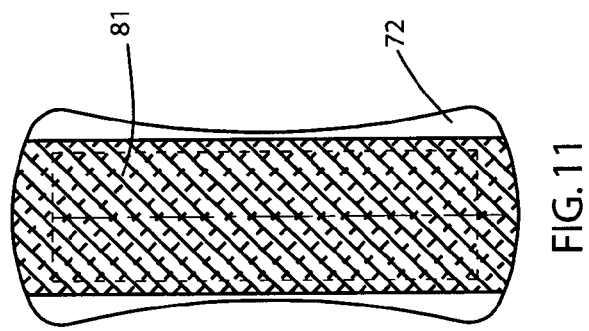
FIG. 11 is a top planar view of one of the fourth pluralities of the sanitary napkins, in accordance with the present invention.
Figure 14:
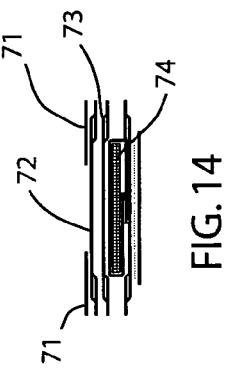
FIG. 14 is a cross sectional, front elevational view of one of the fourth pluralities of sanitary napkins, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The kit of this invention is referred to generally in FIGS. 1-14 by the reference numeral 10 and is intended to provide a plurality of differently sized sanitary napkins for use during different periods of the user menstrual cycle. It should be understood that the kit 10 may be used to protect against many types of leakage, and should not be limited in collecting only those liquids mentioned herein.

Referring initially to FIG. 1, a multi-pack sanitary napkin container includes a flexible outer container 20. Such a container 20 is adjusted in size and shape respectively based upon the number of items contained therein. The container 20 includes a substantially rectangular shaped and planar base 21 with top, bottom, left, and right sides 22, 23, 24, 25 respectively. The container further includes first and second coextensively shaped wings 26, 27 monolithically formed with the left and right sides 24, 25 respectively of the base 21. Each of such first and second wings 26, 27 extends outwardly and away from the base member 21. The container 20 conveniently stores a plurality of sanitary napkins in one easily accessible kit.

The container further includes first and second coextensively shaped walls 28, 29 with bottom edges directly attached, without the use of intervening elements, to the top and bottom sides 22, 23 of the base 21 respectively. Each of such first and second walls 28, 29 has a top edge 30 extending outwardly and away from the base 21. Such top edges 30 have a lateral width that is less than a lateral width of the bottom edges 31, and each of the first and second walls 28, 29 has opposed arcuately shaped outer edges 37 spanning between laterally opposed ends of the top and bottom edges 30, 31 respectively. The top and bottom edges 30, 31 of the first and second walls 28, 29 are oriented parallel to each other.

The container further includes first, second, third, and fourth coextensively shaped flaps 32, 33, 34, 35 with an inner edge 36 monolithically formed with associated ones of the outer edges 37 of the first and second walls 28, 29 respectively. Each of such first, second, third, and fourth flaps 32, 33, 34, 35 has an outer edge 39 extending outwardly and away from the outer edges 37 of the first and second walls 28, 29 respectively. The first and second flaps 32, 33 respectively have a notch 38 formed in the outer edges 39 thereof, and the second flap 33 further has an opening 40 formed therein. The third flap 34 has a tongue 41 monolithically formed in the outer edge 39 thereof and extending outwardly and away from the outer edge 39. The walls and flaps securely house the pluralities of sanitary napkins in one compact space.

The container further includes a tab 43 provided with top and bottom 44, 45 and left and right edges 46, 47 respectively. Such a bottom edge 45 is directly attached, without the use of intervening elements, to the top edge 30 of the first wall 28, and such a top edge 44 of the tab 43 extends outwardly and away from the top edge 30 of the first wall 28. The tab 43 has a lateral width that is equal to the lateral width of the top edge 30 of the first wall 28, and the top edge 44 of the tab 43 and the top edge 30 of the first wall 28 respectively are registered parallel to each other. The tab 43 ensures that the container 20 will remain closed when in storage and in between usages.

The container further includes first, second, and third coextensively shaped flanges 48, 49, 50 monolithically formed with the left, top, and right edges 43, 44, 47 respectively of the tab 43. Each of such first and third flanges 48, 50 has respective longitudinal lengths that are equal to a height of the tab 43, and such a second flange 49 has a longitudinal length that is equal to the lateral width of the tab 43. The container further has first, second, and third panels 51, 52, 53 attached along respective top and bottom longitudinal edges 54, 55 thereof. The top edge 54 of the first panel 51 is monolithically formed with the top edge 30 of the second wall 29, and the top edge 54 of the second panel 52 is monolithically formed with the bottom edge 55 of the first panel 51.

The top edge 54 of the third panel 53 is monolithically formed with the bottom edge 55 of the second panel 52, and the first panel 51 has a longitudinal length that is equal to the lateral width of the top edge 30 of the second wall 29. Each of the first, second, and third panels 51, 52, 53 has equal longitudinal lengths and equal lateral widths respectively, and each of the respective top and bottom edges 54, 55 of the first, second, and third panels 51, 52, 53 is registered parallel to each other. A series of apertures 56 is formed in the top and bottom edges 54, 55 of the first and second panels 51, 52 respectively and the second and third panels 52, 53 respectively. Such apertures 56 are equidistantly spaced along the top and bottom edges 54, 55 of the first and second panels 51, 52 respectively and the second and third panels 52, 53 respectively.

Referring to FIGS. 2, 3, 4, 5, 6, 7, 8, 9 and 10, the kit further includes first, second, third, and fourth pluralities of disposable sanitary napkins 57, 58, 59, 60 vertically stacked within an interior portion of the container 20. The plurality of sanitary napkins provides objects appropriate for various stages of a user menstrual cycle. Each of such first, second, and third pluralities of sanitary napkins 57, 58, 59 respectively includes a top cover stock layer 61 with a pair of tabs 62 monolithically formed in respective upper and lower 63, 64 opposed edges thereof. Such tabs 62 extend outwardly and away from the upper 63 and lower 64 edges respectively. The sanitary napkins further include a pair of side barriers 65 attached to the cover stock layer 61 and situated adjacent to the tabs 62, an acquisition layer 66 attached to the side barriers 65 and disposed medially thereof, and a liquid absorbent core member 67 attached to the acquisition layer 66. Such a core member 67 has a longitudinal length and a lateral width that are respectively less than a longitudinal length and a lateral width of the acquisition layer 66. The core 67 ensures that any liquid is absorbed and thereby ensures that a user will remain dry and comfortable.

The sanitary napkins further include a backsheet 68 positioned about the core member 67. Such a backsheet 68 is suitably sized and shaped which is essential such that the acquisition layer 66 and the core member 67 and the side barriers 65 are respectively intercalated between the backsheet 68 and the cover stock 61. A glue layer 69 is attached to spaced regions along the backsheet 68. Such a glue layer 69 extends beyond an outer perimeter of the core member 67, and a bottom silicon paper layer 70 is attached directly, without the use of intervening elements, to the glue layer 69. The glue layer 69 ensures that the sanitary napkin remains in place during use.

The backsheet 68 and the core member 67 are respectively liquid permeable while the acquisition layer 66 and the side barriers 65 and the cover stock layer 61 are respectively liquid impermeable. Liquid from the user body is transferred to the core member 67 via the liquid permeable layers respectively and penetrates therein. The liquid is absorbed and contained by the core member 67 during operating conditions, thereby ensuring that no staining of a user's panties occurs.

Referring to FIGS. 11, 12, 13 and 14, each of the fourth plurality of sanitary napkins 60 respectively includes a top barrier layer 71 extending about a perimeter of the fourth plurality of sanitary napkins 61 for preventing fluids from traveling beyond the perimeter. A polyethylene layer 72 is attached to the top barrier 71 and extends downwardly therefrom. Such a polyethylene layer 72 is perforated for allowing fluids to enter therethrough. The fourth plurality of sanitary napkins 60 further includes a fabric layer 73 connected to the polyethylene layer 72, an absorbent core 74 connected to the fabric layer 73, a fluid impermeable backsheet layer 75 connected to the absorbent layer 74, a glue layer 80 attached to the backsheet layer 75, and a bottom silicon paper layer 81 removably attached to the glue layer 80. Each of such first, second, third and fourth pluralities of sanitary napkins may be provided with a sanitary wipe removably affixed to said top layer thereof.

Referring to FIG. 1, the kit further includes a mechanism for securing the container about the first, second, third, and fourth pluralities respectively of sanitary napkins 57, 58, 59, 60 when the first, second, third, and fourth pluralities of sanitary napkins 57, 58, 59, 60 are vertically stacked within the interior portion of the container 20. Such a securing mechanism 76 includes a lip 77 monolithically formed with the bottom edge 55 of the third panel 53 and extending outwardly and away therefrom. Such a lip 77 has a longitudinal length that is equal to the longitudinal length of the third panel 53. The securing mechanism 76 further includes a hook-and-loop type fastening material 78 adhered to an inner surface of the lip 77 which is important such that the hook-and-loop type fastening material 78 contacts an outer surface of the covering when the covering is folded about the vertically stacked first, second, third, and fourth pluralities of sanitary napkins 57, 58, 59, 60. Such a fastening material 78 prohibits the container 20 from prematurely and undesirably unfolding during storage and transport procedures. The fastening material 78 may also include buttons, snaps, and zippers. The securing mechanism ensures that the plurality of sanitary napkins remain securely within the container.

The plurality of sanitary napkins provide the unexpected benefit of allowing a user to have every type of sanitary napkin that may be needed during a single menstrual cycle in one convenient package. In addition, the container provides the unexpected benefit of allowing a user to store all of the supplies necessary for a single menstrual cycle in one convenient package. Such benefits overcome the above noted shortcomings.

In use, a method for providing a plurality of differently sized sanitary napkins employed during different periods of a user menstrual cycle includes the steps of: providing a flexible outer container 20; vertically stacking first, second, third, and fourth pluralities of sanitary napkins 57, 58, 59, 60 within an interior portion of the container 20; and securing the container 20 about the first, second, third, and fourth pluralities of sanitary napkins 57, 58, 59, 60 after the first, second, third, and fourth pluralities of sanitary napkins 57, 58, 59, 60 are vertically stacked within the interior portion of the container 20.

In use, the method further includes the steps of providing a lip 77 monolithically formed with the bottom edge 55 of the third panel 53 and extending outwardly and away therefrom. Such a lip 77 has a longitudinal length that is equal to the longitudinal length of the third panel 53. The steps further include providing a fastening material 78 adhered to an inner surface of the lip 77 such that the fastening material 78 contacts an outer surface of the covering when the covering is folded about the vertically stacked first, second, third, and fourth pluralities 57, 58, 59, 60 of sanitary napkins. The fastening material 78 prohibits the container 20 from prematurely and undesirably unfolding during storage and transport procedures.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A multi-pack sanitary napkin container for providing a plurality of differently sized sanitary napkins employed during different periods of a user menstrual cycle, said sanitary napkin container comprising:
    a flexible outer container formed from disposable material;
    first, second, third, and fourth pluralities of disposable sanitary napkins vertically stacked within an interior portion of said container; and
    means for securing said container about said first, second, third, and fourth pluralities of sanitary napkins after said first, second, third, and fourth pluralities of sanitary napkins are vertically stacked within said interior portion of said container;
    wherein said container comprises:
    a generally rectangular and planar base having top, bottom, left, and right sides respectively;
    first and second coextensively shaped wings monolithically formed with said left and right sides respectively of said base, each of said first and second wings extending outwardly and away from said base member; and
    first and second coextensively shaped walls having bottom edges directly attached to said top and bottom sides of said base respectively, each of said first and second walls having a top edge extending outwardly and away from said base, said top edges having a lateral width that is less than a lateral width of said bottom edges, each of said first and second walls having opposed arcuately shaped outer edges spanning between laterally opposed ends of said top and bottom edges respectively, said top and bottom edges of said first and second walls being oriented parallel to each other;
    wherein said container further comprises:
    first, second, third, and fourth coextensively shaped flaps having an inner edge monolithically formed with associated ones of said outer edges of said first and second walls respectively, each of said first, second, third, and fourth flaps having an outer edge extending outwardly and away from said outer edges of said first and second walls respectively, said first and second flaps respectively having a notch formed in said outer edges thereof, said second flap further having an opening formed therein, said third flap having a tongue monolithically formed in said outer edge thereof and extending outwardly and away from said outer edge; and
    a tab provided with top and bottom and left and right edges respectively, said bottom edge being directly attached to said top edge of said first wall, said top edge of said tab extending outwardly and away from said top edge of said first wall, said tab having a lateral width that is equal to said lateral width of said top edge of said first wall, said top edge of said tab and said top edge of said first wall being respectively registered parallel to each other.

2. The sanitary napkin container of claim 1, wherein said container further comprises:
    first, second, and third coextensively shaped flanges monolithically formed with said left, top, and right edges respectively of said tab, each of said first and third flanges having respective longitudinal lengths that are equal to a height of said tab, said second flange having a longitudinal length that is equal to said lateral width of said tab; and
    first, second, and third panels attached along respective top and bottom longitudinal edges thereof, said top edge of said first panel is monolithically formed with said top edge of said second wall, said top edge of said second panel is monolithically formed with said bottom edge of said first panel, said top edge of said third panel is monolithically formed with said bottom edge of said second panel, said first panel having a longitudinal length that is equal to said lateral width of said top edge of said second wall, each of said first, second, and third panels having equal longitudinal lengths and equal lateral widths respectively, each of said respective top and bottom edges of said first, second, and third panels being registered parallel to each other;
    wherein a series of apertures is formed in said top and bottom edges of said first and second panels respectively and said second and third panels respectively, said apertures is equidistantly spaced along said top and bottom edges of said first and second panels respectively and said second and third panels respectively.

3. The sanitary napkin container of claim 2, wherein said securing means comprises:
    a lip monolithically formed with said bottom edge of said third panel and extending outwardly and away therefrom, said lip having a longitudinal length that is equal to said longitudinal length of said third panel; and
    a fastening material adhered to an inner surface of said lip such that said fastening material contacts an outer surface of said covering when said covering is folded about said vertically stacked first, second, third, and fourth pluralities of sanitary napkins;
    wherein said fastening material prohibits said container from prematurely and undesirably unfolding during storage and transport procedures.

4. The sanitary napkin container of claim 1, wherein each of said first, second, and third pluralities of sanitary napkins respectively comprises:
    a top cover stock layer having a pair of tabs monolithically formed in respective upper and lower opposed edges thereof, said tabs extending outwardly and away from said upper and lower edges respectively;
    a pair of side barriers attached to said cover stock layer and situated adjacent to said tabs;
    an acquisition layer attached to said side barriers and disposed medially thereof;
    a liquid absorbent core member attached to said acquisition layer, said core member having a longitudinal length and a lateral width that are respectively less than a longitudinal length and a lateral width of said acquisition layer;
    a backsheet positioned about said core member, said backsheet being suitably sized and shaped such that said acquisition layer and said core member and said side barriers are respectively intercalated between said backsheet and said cover stock;
    a glue layer attached to spaced regions along said backsheet, said glue layer extending beyond an outer perimeter of said core member; and
    a bottom silicon paper layer attached directly to said glue layer.

5. The sanitary napkin container of claim 4, wherein said backsheet said core member are respectively liquid permeable while said acquisition layer and said side barriers and said cover stock layer are respectively liquid impermeable;

wherein liquid from the user body is transferred to said core member via said liquid permeable layers respectively and penetrates therein, said liquid is absorbed and contained by said core member during operating conditions.

6. The sanitary napkin container of claim 5, wherein each of said fourth plurality of sanitary napkins respectively comprises:

a top barrier layer extending about a perimeter of said fourth plurality of sanitary napkins for preventing fluids from traveling beyond the perimeter;

a polyethylene layer attached to said top barrier and extending downwardly therefrom, said polyethylene layer being perforated for allowing fluids to enter therethrough;

a fabric layer connected to said polyethylene layer;

an absorbent core connected to said fabric layer;

a fluid impermeable backsheet layer connected to said absorbent layer;

a glue layer attached to said backsheet layer; and a bottom silicon paper layer removably attached to said glue layer.

7. A method for providing a plurality of differently sized sanitary napkins employed during different periods of a user menstrual cycle, said method comprising the steps of:

a. providing a flexible outer container;

b. vertically stacking first, second, third, and fourth pluralities of sanitary napkins within an interior portion of said container; and c. securing said container about said first, second, third, and fourth pluralities of sanitary napkins after said first, second, third, and fourth pluralities of sanitary napkins are vertically stacked within said interior portion of said container;

wherein said container comprises a generally rectangular and planar base having top, bottom, left, and right sides respectively;

first and second coextensively shaped wings monolithically formed with said left and right sides respectively of said base, each of said first and second wings extending outwardly and away from said base member; and first and second coextensively shaped walls having bottom edges directly attached to said top and bottom sides of said base respectively, each of said first and second walls having a top edge extending outwardly and away from said base, said top edges having a lateral width that is less than a lateral width of said bottom edges, each of said first and second walls having opposed arcuately shaped outer edges spanning between laterally opposed ends of said top and bottom edges respectively, said top and bottom edges of said first and second walls being oriented parallel to each other;

wherein said container further comprises first, second, third, and fourth coextensively shaped flaps having an inner edge monolithically formed with associated ones of said outer edges of said first and second walls respectively, each of said first, second, third, and fourth flaps having an outer edge extending outwardly and away from said outer edges of said first and second walls respectively, said first and second flaps respectively having a notch formed in said outer edges thereof, said second flap further having an opening formed therein, said third flap having a tongue monolithically formed in said outer edge thereof and extending outwardly and away from said outer edge; and a tab provided with top and bottom and left and right edges respectively, said bottom edge being directly attached to said top edge of said first wall, said top edge of said tab extending outwardly and away from said top edge of said first wall, said tab having a lateral width that is equal to said lateral width of said top edge of said first wall, said top edge of said tab and said top edge of said first wall being respectively registered parallel to each other.

8. The method of claim 7, wherein said container further comprises:

first, second, and third coextensively shaped flanges monolithically formed with said left, top, and right edges respectively of said tab, each of said first and third flanges having respective longitudinal lengths that are equal to a height of said tab, said second flange having a longitudinal length that is equal to said lateral width of said tab; and first, second, and third panels attached along respective top and bottom longitudinal edges thereof, said top edge of said first panel is monolithically formed with said top edge of said second wall, said top edge of said second panel is monolithically formed with said bottom edge of said first panel, said top edge of said third panel is monolithically formed with said bottom edge of said second panel, said first panel having a longitudinal length that is equal to said lateral width of said top edge of said second wall, each of said first, second, and third panels having equal longitudinal lengths and equal lateral widths respectively, each of said respective top and bottom edges of said first, second, and third panels being registered parallel to each other;

wherein a series of apertures is formed in said top and bottom edges of said first and second panels respectively and said second and third panels respectively, said apertures is equidistantly spaced along said top and bottom edges of said first and second panels respectively and said second and third panels respectively.

9. The method of claim 8, wherein step c. comprises the steps of:

i. providing a lip monolithically formed with said bottom edge of said third panel and extending outwardly and away therefrom, said lip having a longitudinal length that is equal to said longitudinal length of said third panel; and ii. providing a fastening material adhered to an inner surface of said lip such that said fastening material contacts an outer surface of said covering when said covering is folded about said vertically stacked first, second, third, and fourth pluralities of sanitary napkins;

wherein said fastening material prohibits said container from prematurely and undesirably unfolding during storage and transport procedures.

10. The method of claim 7, wherein each of said first, second, and third pluralities of sanitary napkins respectively comprises:

a top cover stock layer having a pair of tabs monolithically formed in respective upper and lower opposed edges thereof, said tabs extending outwardly and away from said upper and lower edges respectively;

a pair of side barriers attached to said cover stock layer and situated adjacent to said tabs;

an acquisition layer attached to said side barriers and disposed medially thereof;

a liquid absorbent core member attached to said acquisition layer, said core member having a longitudinal length and a lateral width that are respectively less than a longitudinal length and a lateral width of said acquisition layer;

a backsheet positioned about said core member, said backsheet being suitably sized and shaped such that said acquisition layer and said core member and said side barriers are respectively intercalated between said backsheet and said cover stock;
a glue layer attached to spaced regions along said backsheet, said glue layer extending beyond an outer perimeter of said core member; and
a bottom silicon paper layer attached directly to said glue layer.

11. The method of claim 10, wherein said backsheet said core member are respectively liquid permeable while said acquisition layer and said side barriers and said cover stock layer are respectively liquid impermeable;
wherein liquid from the user body is transferred to said core member via said liquid permeable layers respectively and penetrates therein, said liquid is absorbed and contained by said core member during operating conditions.

12. The method of claim 11, wherein each of said fourth plurality of sanitary napkins respectively comprises:
a top barrier layer extending about a perimeter of said fourth plurality of sanitary napkins for preventing fluids from traveling beyond the perimeter;
a polyethylene layer attached to said top barrier and extending downwardly therefrom, said polyethylene layer being perforated for allowing fluids to enter therethrough;
a fabric layer connected to said polyethylene layer;
an absorbent core connected to said fabric layer;
a fluid impermeable backsheet layer connected to said absorbent layer;
a glue layer attached to said backsheet layer; and
a bottom silicon paper layer removably attached to said glue layer.

* * * * *